(12) United States Patent
Lynn et al.

(10) Patent No.: US 8,709,815 B2
(45) Date of Patent: Apr. 29, 2014

(54) SYSTEM AND METHOD FOR THE ANALYSIS OF BIODIESEL

(71) Applicant: Dexsil Corporation, Hamden, CT (US)

(72) Inventors: Theodore B. Lynn, Hamden, CT (US); Lawrence M. Sacramone, Hamden, CT (US)

(73) Assignee: Dexsil Corporation, Hamden, CT (US)

( * ) Notice: Subject to any disclaimer, the term of this patent is extended or adjusted under 35 U.S.C. 154(b) by 0 days.

(21) Appl. No.: 13/665,433

(22) Filed: Oct. 31, 2012

(65) Prior Publication Data

US 2013/0115704 A1    May 9, 2013

Related U.S. Application Data

(60) Provisional application No. 61/555,998, filed on Nov. 4, 2011.

(51) Int. Cl.
*G01N 33/22* (2006.01)
*G01N 21/79* (2006.01)

(52) U.S. Cl.
USPC ........... 436/60; 436/79; 436/129; 436/132; 436/163; 436/174; 436/177; 436/178; 422/430; 422/75

(58) Field of Classification Search
USPC ........... 436/60, 73, 79, 100, 101, 102, 128, 436/129, 131, 132, 163, 164, 166, 174, 177, 436/178; 422/430, 68.1, 75
See application file for complete search history.

(56) References Cited

U.S. PATENT DOCUMENTS

| | | | |
|---|---|---|---|
| 3,980,433 A | | 9/1976 | Tamura et al. |
| 5,545,197 A | * | 8/1996 | Bowen ................. 607/108 |
| 5,596,116 A | * | 1/1997 | Childress et al. .......... 556/427 |
| 7,927,877 B1 | | 4/2011 | Kauffman |
| 2002/0062030 A1 | * | 5/2002 | White et al. ............... 548/204 |
| 2007/0181504 A1 | * | 8/2007 | Binder et al. .............. 210/656 |
| 2009/0316139 A1 | | 12/2009 | Shrestha et al. |
| 2010/0120158 A1 | | 5/2010 | Cummings |
| 2012/0052587 A1 | | 3/2012 | Eldridge et al. |

FOREIGN PATENT DOCUMENTS

WO    2011075420 A1    6/2011

OTHER PUBLICATIONS

ASTM International, Designation: D6751-12, "Standard Specification for Biodiesel Fuel Blend Stock (B100) for Middle Distillate Fuels," pp. 1-10, published Nov. 2012.
ASTM International, Designation: D7371-12, "Standard Test Method for Determination of Biodiesel (Fatty Acid Methyl Esters) Content in Diesel Fuel Oil Using Mid Infrared Spectroscopy (FTIR-ATR-PLS Method)," pp. 1-10, published Jul. 2012.
International Search Report and Written Opinion received for International Application No. PCT/US2012/062767, Date of mailing: Mar. 26, 2013, 9 pages.

* cited by examiner

*Primary Examiner* — Maureen Wallenhorst
(74) *Attorney, Agent, or Firm* — Finch & Maloney PLLC

(57) ABSTRACT

Methods and devices are disclosed providing techniques for measuring the amount of biodiesel in a fuel sample. The methods may be used in the field without the use of laboratory equipment. The biodiesel in the sample is converted to the corresponding free acid which can be isolated and quantified to provide information regarding the amount of biodiesel in the original sample.

20 Claims, 3 Drawing Sheets

SYSTEM AND METHOD FOR THE ANALYSIS OF BIODIESEL

CROSS-REFERENCE TO RELATED APPLICATIONS

This application claims benefit of U.S. Provisional Patent Application Ser. No. 61/555,998, filed on Nov. 4, 2011. Each reference, patent, and patent application and publication cited herein is hereby incorporated by reference in its entirety.

TECHNICAL FIELD

This disclosure relates to biodiesel fuel and methods and devices for analyzing the amount of biodiesel in a petroleum product.

BACKGROUND

Biodiesel (B100) is a mixture of long chain Fatty Acid Methyl Esters (FAME) made from natural fats/oils of either animal or vegetable origin. It is most often blended with diesel fuel refined from petroleum to produce blends of diesel and biodiesel. Blends may include 20% biodiesel (B20), 5% biodiesel (B5), or 1% biodiesel (B1). These blends are then combusted in internal combustion engines to power vehicles, electrical generators and the like. Similar blends may also be used as a heating fuel.

The introduction of biodiesel into the fuel stream has led to an additional need for testing for contaminants, such as free acid, mono & diglycerides, glycerin, leftover catalyst and water. ASTM biodiesel standard D-6751 covers specifications for B100 or the pure FAME mixture produced from the bio feedstock. Tests for the amount of B100 in fuel blends are typically performed in the laboratory and include a laboratory test for biodiesel content in diesel fuel blends based on FTIR analysis (ASTM D-7371).

SUMMARY OF THE INVENTION

In one or more embodiments, a method of analyzing fuel for biodiesel content is provided that includes converting at least a portion of any methyl esters present in a fuel sample to the corresponding free acid, reacting the free acid with a strong acid to protonate the free acid, solubilizing the protonated tree acid in a non-polar fluid, and measuring the protonated free acid in the non-polar fluid to determine the concentration of methyl esters in the fuel. The sample may be heated either in the presence of a strong base or an alcohol to convert the methyl esters to the corresponding free acid. This may be achieved either via an external heat source or by a chemical reaction. The chemical reaction may be an in situ reaction, for example, a reaction of an alkali metal and a compound comprising a hydroxyl group. In some instances, the compound may comprise either an alcohol or ethanol. In some embodiments, the alkali metal may be reacted with water. In some instances, the alkali metal may be metallic sodium.

In some embodiments, the protonated free acid may be titrated or back titrated to a colorimetric end point to determine the concentration of methyl esters in the fuel. In some instances, the method may include concentrating the methyl esters prior to converting to the free acid. In some example instances, the methyl esters may be concentrated by adsorbing onto a solid phase. In some example instances, the methyl esters are returned to a liquid phase prior to converting to the free acid. In one or more embodiments, the methyl esters are fatty acid methyl esters. In some embodiments, the free acid is a carboxylic acid.

In one or more embodiments, a test kit for analyzing fuel for biodiesel content is provided that includes a sampling device for taking an accurately sized fuel sample, a heating device for converting at least a portion of any methyl esters present in a fuel sample to the corresponding free acid, at least one ampule containing a strong base and/or an alcoholic solvent to help improve the rate of conversion, a strong acid to help protonate the free acid, and a non-polar fluid to help solubilize the protonated free acid. In some embodiments, the heating device is an alkali metal that heats by causing a chemical reaction with the fuel sample. In some instances, the test kit may include titrant to help determine the concentration of methyl esters in the fuel. In one or more embodiments, the test kit may include instructions for analyzing fuel for biodiesel content.

The systems, devices and methods described herein may be used separately or together, and components or techniques described in relation to one system or method are capable of being implemented with the others. The subject matter of this application may involve, in some cases, interrelated products, alternative solutions to a particular problem, and/or a plurality of different uses of a single system or article.

BRIEF DESCRIPTION OF THE DRAWINGS

The above-mentioned and other features of this disclosure, and the manner of attaining them, will become more apparent and better understood by reference to the following description of embodiments described herein taken in conjunction with the accompanying drawings, wherein.

DETAILED DESCRIPTION

Figure 1:
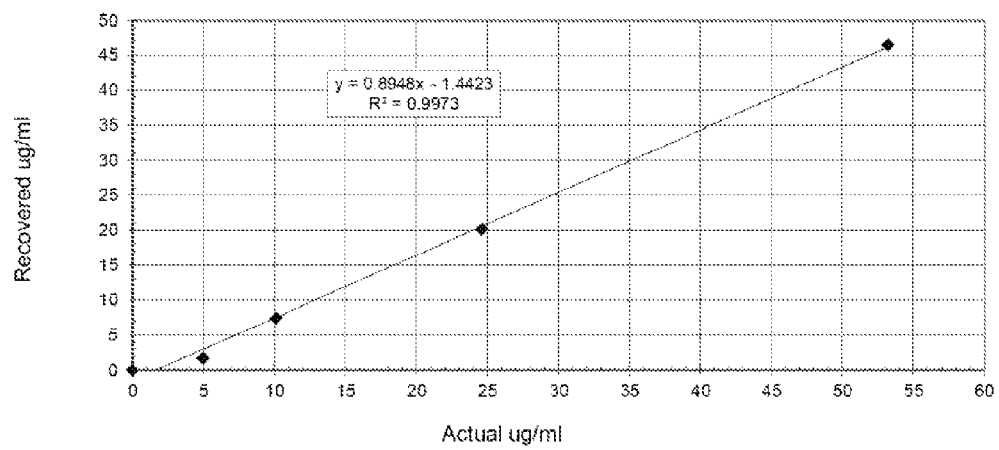
FIG. 1 provides a graph showing results from an experiment comparing spiked concentrations of biodiesel with measured concentrations.

Once a biodiesel blend is made, the mixture is visibly indistinguishable from diesel of 100% petroleum origin. As a result, tests are necessary to verify the biodiesel or "bio" content of the blend. Described herein are methods and devices for field determination of the bio content of a biodiesel blend. The test may also be useful in other fuels and in non-fuel hydrocarbons.

Of particular concern in the aviation field is the inadvertent contamination of jet fuel with FAME. This can occur in tank farms at airports when transporting different fuels via multi-product pipelines. Currently the acceptable level of FAME in jet fuel is 5 ppm. FTIR methods are not sensitive enough to reach these detection limits, but GC and GC-MS methods can detect FAME down to these levels. However, these techniques require expensive instrumentation and highly trained personnel.

In one aspect of the disclosure, a method of determining the level of FAME in a biodiesel blend is provided. The method can be performed quickly outside of the laboratory environment by operators of various levels of training. In an initial step, the fuel sample may be heated in the presence of a strong base and an alcohol. This reaction converts any long chain methyl esters to the corresponding free acid, typically a carboxylic acid. The tree acid may be in its deprotonated form and can form an emulsion with the non-polar fuel sample. To accurately measure the amount of free acid, the sample can be washed with an aqueous acid such as HCl or $H_2SO_4$ to neutralize any excess base and to protonate the free acid. This can break the emulsion and the protonated free acid species can partition to the organic layer. The organic layer then contains a concentration of protonated free acid that is proportional to the amount of FAME originally present in the sample. The acid content of the organic layer can be measured directly or it can be titrated to determine the amount of acid present. The sample may be titrated or back titrated and may be titrated directly or first extracted into a separate aqueous phase. Knowing the average equivalent weight of the FAME molecules and the dilution/concentration factors that may be included in the process, the titration results may be correlated to the FAME concentration of the original fuel sample, thus providing the percentage of biodiesel in the fuel.

In one set of embodiments the fuel sample is reacted with a base in the presence of an alcohol at an elevated temperature. The FAME produced from vegetable and animal products to make biodiesel has a molecular weight that can range from 158 to 353 with the majority of commercially important sources having a distribution between 214 and 292. The base used should be strong enough to convert the FAME to the corresponding free acid, and the base may be a strong base such as sodium hydroxide or potassium hydroxide. The base may be applied in an adequate amount, or greater than adequate amount, to convert the anticipated amount of FAME to the corresponding acid. For example, the equivalents of base used may be 1, 2, 5 or more than 10 times the anticipated number of equivalents of FAME present in the fuel sample. The concentration of the base may be great enough to allow for an adequate amount of base at a small volume. For instance, in some embodiments the base solution used may be 0.1 M, 0.4 M or 1 M. The temperature at which the methyl esters are converted may be greater than room temperature and may be, for example, greater than 30° C., greater than 50° C., greater than 70° C. or greater than 90° C. Samples may be heated via an external heat source such as a hot plate or can be heated by a chemical reaction in situ. Depending on temperature and reactants, the reaction may continue for more than 5 minutes, more than 15 minutes, more than 30 minutes or greater to provide a complete or essentially complete conversion of the methyl esters.

To promote conversion of the FAME to the corresponding acids it has been found that the presence of an alcohol improves the rate of reaction. The alcohol may be aliphatic or aromatic and is preferably a lower molecular weight aliphatic alcohol such as methanol or ethanol. The alcohol may act as a diluent as well as a catalyst. The alcohol may be, for instance, 10, 20, 30, 40 or 50 percent, by weight, of the reaction medium. For instance, 8 grams of fuel may be mixed with 2 grams of ethanol to make a 20% ethanol in fuel mixture. The alcohol may also act as a carrier for the base. For instance, an alcoholic KOH solution may be added to the fuel to provide diluent, reactant and catalyst together in a single phase.

To measure the amount of acid present after conversion of any FAME, it may be helpful to protonate the free acid to facilitate separation of the acid from other aqueous species that can interfere with the analysis. This protonation step can be performed by adding an acid to the post-reaction mixture. For example, a mineral acid such as HCl or $H_2SO_4$ may be mixed with the reacted fuel in order to protonate the long chain acids that have been produced. The acid can neutralize any residual base and can also protonate the long chain acids that are present. Thus, the amount of acid used should be enough to neutralize any leftover base and to protonate any acids that have been formed. For example, the acid may be 0.1 N, 0.5 N, 1.0 N or greater. The volume of acid added may be equal to, greater than, or a fraction of the amount of organic phase present. For example, 5 mL of a 0.8 N solution of HCl can be added to 5 mL of reacted fuel. After addition, the sample may be agitated by, for example, shaking, and then allowed to settle into two distinct phases.

After separation into organic and aqueous phases, the majority of the protonated acids will be in the organic phase. Other water soluble species will partition to the aqueous phase and thus be separated from the acids derived from the FAME. By analyzing this organic phase, the amount of acid derived from FAME can be determined.

In one set of embodiments the acid in the organic phase can be detected without the aid of instrumentation. For instance, the organic phase can be titrated against a base colorimetrically in the presence of a pH indicator. Alternatively, a portion of the organic phase can be reacted with an excess of base and then the residual base can be back titrated with an acid. Either process can inform the operator of the amount of acid in the organic phase. By tracking the quantities reacted in each step, the original concentration of FAME in the fuel sample can be accurately determined.

In one set of embodiments the heat for converting the FAME to the corresponding acids can be provided by a chemical reaction. The chemical reaction may take place directly in the fuel sample. For example, an alkali metal can be reacted with water or an organic compound that includes a hydroxyl group. The resulting reaction is exothermic and can raise the temperature of the fuel sample to greater than 30° C., greater than 50° C. or greater than 70° C. The resulting reaction can also convert the alcohol to a corresponding alkoxide. For instance, ethanol can be converted to ethoxide which then is capable of catalyzing an ester exchange, which in the presence of the hydroxide ions can result in a complete or almost complete conversion to the more stable carboxylate anion. Therefore, the use of an alkali metal not only provides important reactants but also the beat necessary to bring the reaction to completion in an acceptable time frame. In some cases the alkali metal can be in the form of an organic dispersion and may be, for example, metallic sodium dispersed in mineral oil.

When detection limits below the percentage level are needed, the FAME content of a sample may be concentrated by adsorbing the esters onto a solid phase and then eluting into a liquid phase at a higher concentration than in the original sample. For instance, biodiesel contamination in jet fuel is carefully monitored for even part per million levels of FAME in the fuel. A jet fuel sample may be contacted with an adsorbent by, for example, mixing the fuel with an adsorbent or by passing the fuel sample over a column of adsorbent. The adsorbent may be any material that cart efficiently adsorb FAME while not having a specific affinity for hydrocarbons. Adsorbents may include, for example, silica gel, alumina and Florisil. In one set of embodiments a column containing Florisil has been found to efficiently remove the methyl esters from the fuel sample. After passing a volume of fuel over the adsorbent, the methyl esters can be desorbed via a solvent or cosolvents with an affinity for FAME. Cosolvents may be, for example, a mixture of a hydrocarbon and an alcohol. In some embodiments, a cosolvent of 20% ethanol in isooctane has been found to provide adequate removal of FAME from the adsorbent. By knowing how much fuel was passed through the adsorbent column and how much solvent was required to elute the adsorbed FAME, one of skill in the art is able to determine the concentration factor. Thus if the concentration factor is known, the concentration of FAME in the eluate can be used to determine the amount of FAME in the original hydrocarbon sample.

Detection of biodiesel (FAME) can be either quantitative or qualitative. For example, a titrating syringe can include indicia that indicate a level of FAME in the original fuel sample when prescribed quantities and procedures are followed. The test can also be run on a go/no go basis where the free acid is titrated with a fixed amount of base that corresponds to a specific threshold such as 20%, 10% or 5 ppm of FAME, depending on the specific application. If a color change occurs, then the sample will be deemed to have either passed or failed, depending on whether a color change indicates that the sample is over or under the threshold. For instance, if the threshold level of biodiesel in Jet A is 5 ppm, then a color change that occurs after introducing a fixed amount of base would indicate that the original fuel sample contains less than 5 ppm and is rated "pass." If no color change occurs, then the sample would be rated "fail" because it contains greater than the threshold amount of biodiesel.

In one set of embodiments a test kit is provided in which reagents and materials can be pre-packaged for use in the field. A heating plate or other heating device can be included and in some cases a stirring device such as a magnetic stirrer can be included. The kit may include a sampling device, such as a volumetric syringe, for taking an accurately sized fuel sample. The kit may also include an alcoholic solvent, a fixed amount of strong base and an alkali metal. These reagents may be provided in crushable glass ampules allowing the reagents to be introduced by breaking the ampules inside a flexible plastic test tube. Each of these reagents may be sealed in a glass ampule or test tube. Titrant may be provided in a plastic syringe that includes indicia indicating the amount of titrant used. Indicia may also indicate directly the amount of biodiesel in the sample being tested. The kit may also contain instructions for use.

EXAMPLES

The following experiments show how the method can be run to detect various levels of biodiesel in different fuels. The experiments provide results that indicate the efficacy of the methods and show the use of a concentrating adsorbent. Data also indicate minimum detection limits and provide values for accuracy of the methods.

Example 1

To simulate the contamination of jet fuel with biodiesel a sample of Jet A was spiked with methyloleate at concentrations of 5, 10, 25 and 50 ppm (precise concentrations provided below in Table 1). A 50 mL sample of the spiked fuel was passed through a column containing 2.6 g Florisil at 3 mL per minute using a 60 mL polypropylene syringe. The column was then washed with 10 mL of isooctane. The adsorbed methyloleate was then desorbed by passing 10 mL of 80/20 isooctane/ethanol through the column, discarding the first 2 mL and the last 4.5 mL. The middle 3.5 mL of eluate were added to a 15 mL glass vial containing a magnetic stir bar. To this vial was added 0.4 mL of 9.49 M KOH. The cap was tightened and the solution was stirred for 30 minutes at 70° C. The solution was allowed to cool and 5 mL of 0.81 N HCl was added. The mixture was shaken for two minutes and allowed to settle for 10 minutes. The mixture separated into two distinct layers and 2 mL of the top organic layer was removed and placed in a polyethylene test tube. To this 2 mL portion was added 0.1 mL of a pH indicator solution made from 0.8% w/v thymolphthalein in 99.5% ethanol and 0.5% water. The resulting solution was titrated to a light blue end point with 0.003 N KOH. Results showing the amount detected vs. the theoretical amounts are provided in Table 1 and FIG. 1. Results were calculated by taking into account the various dilution and concentration steps during the process.

TABLE 1

| Sample ID | Methyloleate µg/mL Actual | Recovered Methyloleate µg/mL |
|---|---|---|
| Blank | 0.00 | 0.00 |
| 1 | 4.94 | 1.74 |
| 2 | 10.07 | 7.46 |
| 3 | 24.60 | 20.14 |
| 4 | 53.20 | 46.50 |

Example 2

Figure 2:
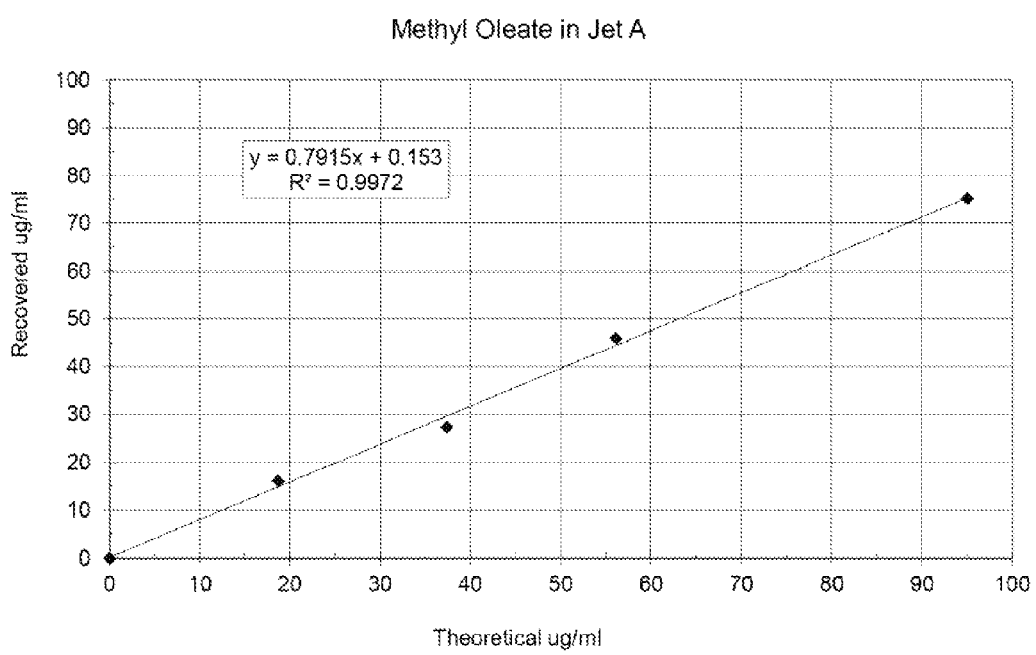
FIG. 2 provides a graph showing results from a second experiment comparing spiked concentrations of biodiesel with measured concentrations.

The experiment of Example 1 was repeated using a 93.5 µg/mL methyloleate in Jet A standard. The column was charged with different amounts of the Jet A standard to provide a range of methyloleate in Jet A representing contamination levels from 0 to 95 µg/mL. Contamination levels and results are provided in Table 2 and FIG. 2.

TABLE 2

| Sample ID | Actual µg/mL methyloleate | Detected mEqs methyloleate | Detected µg/mL methyloleate |
|---|---|---|---|
| Blank | 0 | 0 | 0.0 |
| 1 | 18.7 | 0.00274 | 16.2 |
| 2 | 37.4 | 0.00462 | 27.4 |
| 3 | 56.1 | 0.00777 | 46.0 |
| 4 | 95 | 0.0127 | 75.2 |

Example 3

Figure 3:
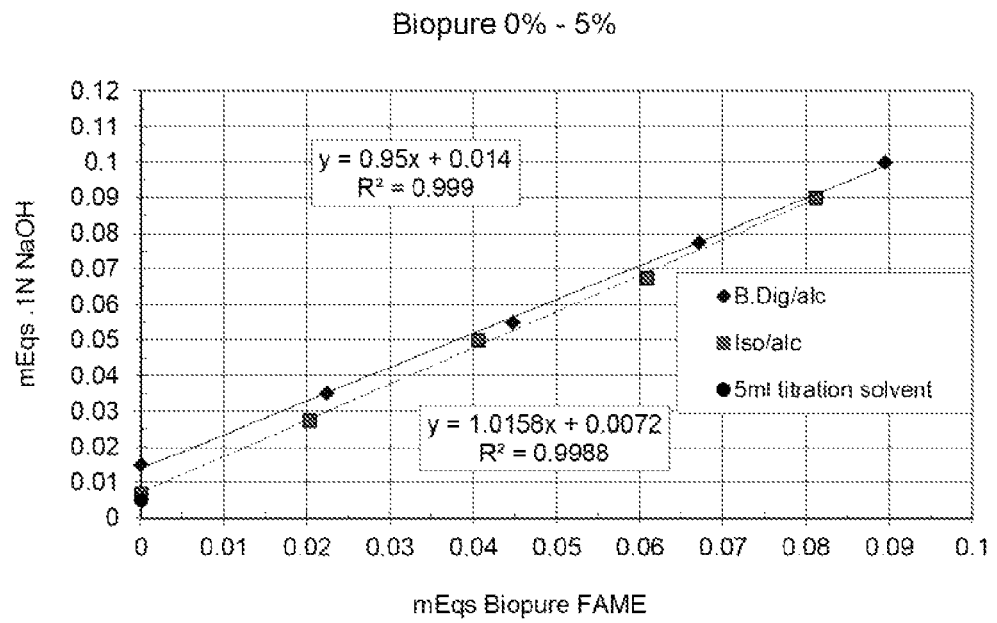
FIG. 3 provides a graph showing results from a third experiment comparing spiked concentrations of biodiesel with measured concentrations.

Another experiment was run without concentrating the methyl ester on an adsorbent. Two different solvent systems were tested to determine which one provides the better result. Cosolvent 1 was an 80/20 v/v mixture of isooctane and ethanol. Cosolvent 2 was a 70/30 v/v mixture of diethylene glycol dibutyl ether (butyl diglyme) and ethanol. Samples of pure diesel were spiked with B100 at levels of from 0 to 5% as shown in Table 3. A 1 mL aliquot of each sample was dissolved in 3.3 mL of cosolvents and reacted with 0.4 mL of 9.49 M KOH, as above. After cooling, 5 mL of 1.5 N HCl/ 20% NaCl was added and the mixture was shaken for two minutes prior to settling for 10 minutes. Two mL of the organic layer was removed and mixed with 5 mL of a titration solvent made from 125 mL alcohol, 0.03 g thymophthalein and 0.5 mL DI water. Each sample was titrated with 0.10 N NaOH to a light blue end point. The amount of NaOH titrated was then used to back calculate the amount of B100 present in the spiked samples. Detected levels were compared to theoretical levels. Results are provided in Table 3 and FIG. 3.

TABLE 3

| Sample ID | Cosolvent Used | Spiked level of B100 % by Volume | mEq of B100 w Titration | Detected Level of B100 |
|---|---|---|---|---|
| Blank | Isooctane/ethanol | 0 | 0 | 0.007 |
| 2 | Isooctane/ethanol | 1.25 | 0.02028 | 0.0275 |
| 3 | Isooctane/ethanol | 2.50 | 0.040559 | 0.05 |
| 4 | Isooctane/ethanol | 3.75 | 0.060839 | 0.0675 |
| 5 | Isooctane/ethanol | 5.0 | 0.081118 | 0.09 |
| Blank | Butyl Diglyme/ethanol | 0 | 0 | 0.015 |
| 7 | Butyl Diglyme/ethanol | 1.25 | 0.0224 | 0.035 |
| 8 | Butyl Diglyme/ethanol | 2.50 | 0.0447 | 0.055 |
| 9 | Butyl Diglyme/ethanol | 1.75 | 0.0671 | 0.0775 |
| 10 | Butyl Diglyme/ethanol | 5.0 | 0.0895 | 0.1 |

Example 4

Figure 4:
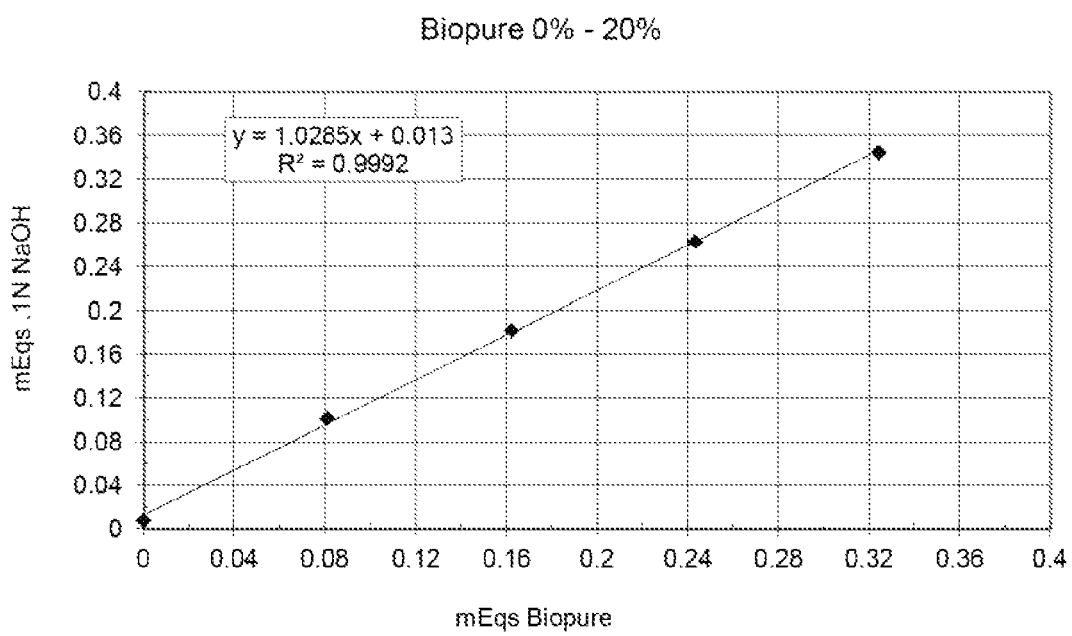
FIG. 4 provides a graph showing results from a fourth experiment comparing spiked concentrations of biodiesel with measured concentrations.

The procedure of Example 3 was repeated on petroleum diesel fuel samples spiked with B100 at levels of 0, 5, 10, 15 and 20% by volume. The cosolvent used was 80/20 v/v isooctane/ethanol. Results axe provided in Table 4 and graphically in FIG. 4.

TABLE 4

| Sample and Concentration | B100 MEq in Titration | Measured B100 mEq |
|---|---|---|
| Blank | 0 | 0.0081 |
| 1-5% | 0.081118 | 0.10125 |
| 2-10% | 0.162236 | 0.18225 |
| 3-15% | 0.243355 | 0.26325 |
| 4-20% | 0.324473 | 0.34425 |

Example 5

To determine the Minimum Detection Limit (MDL) for this method, a 1% biodiesel in diesel sample was analyzed seven times to determine the variation. The method of Example 4 was used. Results were titrated using 10 μL titration increments of 0.1 N NaOH. At this resolution each sample reached an endpoint at 60 μL of 0.405 N NaOH (0.0243 mEq). There was no variation in the results for the seven repeat samples. The rate of color change may be the source of greatest variation and the titrations indicated that the total resolution of the method is approximately 0.2%.

Example 6

Figure 5:
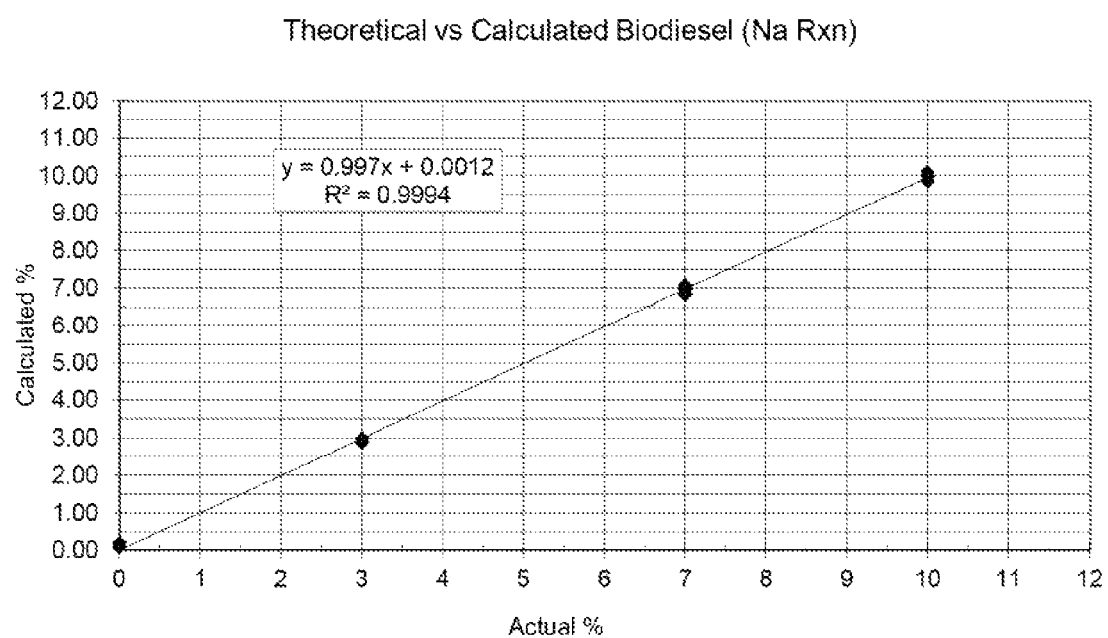
FIG. 5 provides a graph showing results from a fifth experiment comparing spiked concentrations of biodiesel with measured concentrations.

To demonstrate the efficacy of using an alkali metal to aid in the conversion of FAME to the free acid, an experiment was run in which sodium metal was used to test biodiesel blends ranging from 0 to 10%. After preparing samples to the prescribed concentrations, 0.775 mL of each sample was placed in a flexible polyethylene test tube. A glass ampule containing 2 mL of 46.3% butyl diglyme, 46.3% ethanol and 7.4% DI water, by volume, was broken in the presence of the sample to introduce the sample to the solvent mixture. The tube was capped and shaken for 30 seconds. An ampule containing 3 mEq of ground sodium metal suspended in mineral oil was broken in the test tube and the mixture was shaken for 1 minute. No external source of heat was provided. The tube was vented and allowed to stand for 9 minutes. To this mixture was added 5 mL of 1.5 N HCl and 1 mL of isooctane. The tube was covered and shaken for two minutes and then allowed to settle for 5 minutes. The mixture separated into an upper organic layer and a lower aqueous layer. One mL of the organic layer was removed and placed in a second polyethylene tube containing 2.5 mL of a titration solvent made my dissolving 0.03 g thymolphthalein and 0.5 mL DI water in 125 mL absolute ethanol. A polypropylene syringe filled with 1 mL of 0.07 N NaOH and fitted with a half inch 30 gauge blunt tipped needle was used to titrate the solution to a light blue end point. The syringe included printed indicia to indicate the amount of titrant dispensed into the tube in order to reach the end point. The amount of FAME present in the diesel samples was then calculated by applying the dilution factors occurring during the various steps of the procedure. Results are provided in Table 5 and FIG. 5. The correlation coefficient was almost 1 and the precision within replicates was about 0.25%. The results indicate that the use of an alkali metal can provide enough heat and catalysis to convert or substantially convert the methyl esters to the corresponding free acid. This is in contrast to experiments run in the absence of heat which show little or no conversion of the esters.

TABLE 5

| Sample ID | Biodiesel Concentration v % | Titrant vol (mL) | Measured Concentration v % | Standard Deviation | 2 Standard Deviations |
|---|---|---|---|---|---|
| 1 | 0 | 0.07 | −0.04 | | |
| 2 | 0 | 0.09 | 0.20 | | |
| 3 | 0 | 0.06 | −0.15 | | |
| 4 | 0 | 0.08 | 0.08 | 0.1504 | 0.3007 |
| 5 | 3 | 0.32 | 2.88 | | |
| 6 | 3 | 0.33 | 2.99 | | |
| 7 | 3 | 0.33 | 2.99 | | |
| 8 | 3 | 0.33 | 2.99 | 0.0582 | 0.1165 |
| 9 | 7 | 0.67 | 6.95 | | |
| 10 | 7 | 0.68 | 7.07 | | |
| 11 | 7 | 0.68 | 7.07 | | |
| 12 | 7 | 0.66 | 6.84 | 0.1115 | 0.223 |
| 13 | 10 | 0.94 | 10.10 | | |
| 14 | 10 | 0.92 | 9.86 | | |
| 15 | 10 | 0.93 | 9.98 | | |
| 16 | 10 | 0.93 | 9.98 | 0.0951 | 0.1902 |

While several embodiments of the present invention have been described and illustrated herein, those of ordinary skill in the art will readily envision a variety of other means and/or structures for performing the functions and or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

What is claimed is:

1. A method of analyzing fuel for biodiesel content, the method comprising:
   converting at least a portion of any methyl esters present in a fuel sample to a corresponding free acid;
   reacting the free acid with a strong acid to protonate the free acid;
   forming an aqueous phase and a separate organic phase, the protonated free acid being solubilized in the organic phase; and
   measuring the protonated free acid in the organic phase to determine the concentration of methyl esters in the fuel.

2. The method of claim 1, wherein the fuel sample is heated in the presence of a strong base to convert the methyl esters to the corresponding free acid.

3. The method of claim 1, wherein the fuel sample is heated in the presence of an alcohol to convert the methyl esters to the corresponding free acid.

4. The method of claim 1, wherein the fuel sample is heated by a chemical reaction to convert the methyl esters to the corresponding free acid.

5. The method of claim 4, wherein the chemical reaction is an in situ reaction of an alkali metal and a compound comprising a hydroxyl group.

6. The method of claim 5, wherein the compound comprises an alcohol.

7. The method of claim 5, wherein the compound comprises ethanol.

8. The method of claim 5, comprising reacting water with the alkali metal.

9. The method of claim 5, wherein the alkali metal is metallic sodium.

10. The method of claim 1, wherein the protonated free acid is titrated to a colorimetric end point to determine the concentration of methyl esters in the fuel.

11. The method of claim 1, wherein the protonated free acid is back titrated to a colorimetric end point to determine the concentration of methyl esters in the fuel.

12. The method of claim 1, further comprising concentrating the methyl esters prior to converting to the free acid.

13. The method of claim 12, wherein the methyl esters are concentrated by adsorbing onto a solid phase.

14. The method of claim 13, wherein the methyl esters are returned to a liquid phase prior to converting to the free acid.

15. The method of claim 1, wherein the methyl esters are fatty acid methyl esters.

16. The method of claim 1, wherein the free acid is a carboxylic acid.

17. A test kit for analyzing fuel for biodiesel content, comprising:
   a sampling device for taking an accurately sized fuel sample;
   a heating device for converting at least a portion of any methyl esters present in a fuel sample to a corresponding free acid;
   at least one ampule containing a strong base and/or an alcoholic solvent;
   a strong acid in aqueous solution to help protonate the free acid; and
   a non-polar fluid to help solubilize the protonated free acid.

18. The test kit of claim 17, wherein the heating device is an alkali metal that heats via a chemical reaction.

19. The test kit of claim 17, further comprising titrant to help determine the concentration of methyl esters in the fuel.

20. The test kit of claim 17, further comprising instructions for analyzing fuel for biodiesel content.

* * * * *